(12) United States Patent
Tracton et al.

(10) Patent No.: US 8,368,892 B2
(45) Date of Patent: Feb. 5, 2013

(54) INFRARED SPECTROSCOPY

(75) Inventors: Kenneth Tracton, Palo Alto, CA (US);
Quinn Jacobson, Sunnyvale, CA (US)

(73) Assignee: Nokia Corporation, Espoo (FI)

( * ) Notice: Subject to any disclaimer, the term of this patent is extended or adjusted under 35 U.S.C. 154(b) by 332 days.

(21) Appl. No.: 12/695,463

(22) Filed: Jan. 28, 2010

(65) Prior Publication Data

US 2011/0181867 A1    Jul. 28, 2011

(51) Int. Cl.
*G01N 21/00* (2006.01)
(52) U.S. Cl. .......... 356/432; 356/51; 356/328; 356/456; 356/323
(58) Field of Classification Search .................... 356/51, 356/328, 432, 435, 437
See application file for complete search history.

(56) References Cited

U.S. PATENT DOCUMENTS

| | | | | |
|---|---|---|---|---|
| 3,390,605 | A * | 7/1968 | Nagamura | 356/73 |
| 6,040,915 | A * | 3/2000 | Wu et al. | 356/435 |
| 6,636,316 | B1 * | 10/2003 | Matsumoto et al. | 356/437 |
| 7,196,789 | B2 * | 3/2007 | Senturia et al. | 356/323 |
| 2009/0124918 | A1 | 5/2009 | Stockmann et al. | 600/532 |
| 2009/0227287 | A1 | 9/2009 | Kotidis | 455/556.1 |

FOREIGN PATENT DOCUMENTS

| | | |
|---|---|---|
| EP | 1 111 369 B1 | 5/2005 |
| WO | WO 00/55602 | 9/2000 |
| WO | WO 2006/127840 A2 | 11/2006 |
| WO | WO 2008/134134 A1 | 11/2008 |
| WO | WO 2009/101374 A1 | 8/2009 |

OTHER PUBLICATIONS

"A Comparison of Rare-Gas Flashlamps", John Oliver and Frank S. Barnes, IEEE Journal of Quantum Electronics, vol. QE5, No. May 5, 1969 (pp. 232-237).
"Abstract for Measuring Liquid Material Component Content by Near-Infrared Spectrum", http://218.240.13.210/sipo_EN/search/detail.do?method=view&parm=16b414c2 . . . (1 page).

(Continued)

Primary Examiner — Tarifur Chowdhury
Assistant Examiner — Isiaka Akanbi
(74) Attorney, Agent, or Firm — Harrington & Smith

(57) ABSTRACT

An apparatus includes an optical source providing an optical beam; a splitter configured to split the optical beam into a sample beam and a reference beam; a sample path containing a sample material to be analyzed, the sample beam being directed through the sample path so as to interact with the sample material; a reference path containing a reference material, the reference beam being directed through the reference path so as to interact with the reference material; a disperser configured to receive the sample beam after it exits the sample path and to receive the reference beam after it exits the reference path, the disperser outputting a dispersed sample beam and a dispersed reference beam; and a photodetector disposed to receive the dispersed sample beam and the dispersed reference beam and outputting electrical signals comprised of data indicative of a spectra of the sample beam after it exits the sample path and a spectra of the reference beam after it exits the reference path. In one embodiment the apparatus further includes a data processor connected with a memory storing a software program configured to process the data to detect a presence of at least one type of molecular species that includes the sample material; and a transmitter configured to transmit the processed data to a receiver. In another embodiment the apparatus includes a transmitter configured to transmit the data to a remote receiver for processing.

20 Claims, 3 Drawing Sheets

OTHER PUBLICATIONS

"A Gamma Ray Spectrometer Based on Mobile Phone Technology", Moss, et al, http://adsabs.hardvard.edu/abs/2006APS..DNP.3A057M.

"Mobile-R Portable FT-IR Spectrometer", Bruker Optics (2 pages).

"Use of Open-Path FTIR Spectroscopy to Address Air Monitoring Needs During Site Remediations", Minnich, et al, (pp. 1-16) (1999).

"Part 1: Imaging Spectroscopy: From Air Quality Investigations to Healthcare Applications,Part 2: Chemical Ionisation Reaction Mass Spectrometry (CIR-MS) For Breath, Analysis Research", University of Leicester, Roland Leigh. Mar. 12, 2009 (27 Pages).

"Measuring Air Quality" http://www.ace.mmu.ac.uk/eae/Air_quality/Older/Print/Measuring.html, (1 page).

* cited by examiner

INFRARED SPECTROSCOPY

TECHNICAL FIELD

The exemplary and non-limiting embodiments of this invention relate generally to optical spectroscopy and, more specifically, relate to infrared spectroscopy of gaseous samples.

BACKGROUND

This section is intended to provide a background or context to the invention that is recited in the claims. The description herein may include concepts that could be pursued, but are not necessarily ones that have been previously conceived, implemented or described. Therefore, unless otherwise indicated herein, what is described in this section is not prior art to the description and claims in this application and is not admitted to be prior art by inclusion in this section.

An important aspect of pollution and air constituent detection is an ability to determine the identities of the compounds that are suspected of being the components of the air sample under observation.

One technique to determine the presence of certain compounds in a sample of a gas (e.g., air) is to use spectrometry, spectroscopic techniques and spectroscopic methods. This technique determines the presence and concentration of a given element or compound in a sample via the interaction of energy with the sample. The device that is used is known as a spectrometer or spectrograph. Spectroscopy is a staple of physical or analytical chemistry in the identification of substances through the spectrum emitted from or absorbed by substances that compose the sample.

The data obtained from the use of spectroscopy is referred to as a spectrum. A spectrum is a plot of the intensity of energy detected versus the wavelength (mass, momentum or frequency) of the energy. A spectrum can be used to discover information about the atomic and molecular energy levels, molecular geometry, chemical bonds, the interaction of molecules and related processes. The spectrum can be used to identify (qualitative analysis) the components of a sample. The spectrum can also be used to determine the amount of material (quantitative analysis) in a sample.

A spectroscope typically includes an energy source (commonly a laser) and a device for measuring the change in the energy emitted from the source after it has interacted with the sample. Conversely the sample may be induced to emit light, thereby negating the need for an external light source. The detection portion of the spectroscope is referred to typically as a spectrophotometer.

Mobile devices have been used to aid in the collection data regarding airborne substances, such as those typically associated with sources of pollution. This type of collection basically includes three major steps: (a) collect a sample, (b) determine an interaction of the sample with an energy source, and (c) transmit the result to a server for data analysis. Collection is not particularly difficult as the gases or particles being studied are airborne. Transmission of the result data to the server by the mobile device is also straightforward, as the transmission can occur using standardized wireless (e.g., cellular) interfaces. However, the second step (determination of the sample properties) presents a significant problem.

The most straight forward method would be to employ spectroscopic examination. However, currently available spectroscopes are bulky, sensitive and not designed for use in the field. There are smaller versions available, such as alpha particle or accelerated proton spectrographs, but these devices tend to be expensive and operate using undesirable radiation.

SUMMARY

The foregoing and other problems are overcome, and other advantages are realized, in accordance with the exemplary embodiments of this invention.

In a first aspect thereof the exemplary embodiments provide an apparatus that includes an optical source providing an optical beam; a splitter configured to split the optical beam into a sample beam and a reference beam; a sample path containing a sample material to be analyzed, said sample beam being directed through said sample path so as to interact with said sample material; a reference path containing a reference material, said reference beam being directed through said reference path so as to interact with said reference material; a disperser configured to receive said sample beam after it exits the sample path and to receive said reference beam after it exits the reference path, said disperser outputting a dispersed sample beam and a dispersed reference beam; and a photodetector disposed to receive the dispersed sample beam and the dispersed reference beam and outputting electrical signals comprised of data indicative of a spectra of the sample beam after it exits the sample path and a spectra of the reference beam after it exits the reference path.

In a further aspect thereof the exemplary embodiments provide a method that includes outputting an optical beam from an optical source; splitting the optical beam into a sample beam and a reference beam; directing the sample beam through a sample path containing a sample material to be analyzed so as to interact with said sample material; simultaneously directing the reference beam through a reference path containing a reference material so as to interact with said reference material; dispersing said sample beam after it exits the sample path and said reference beam after it exits the reference path and outputting a dispersed sample beam and a dispersed reference beam; and generating electrical signals from said dispersed sample beam and said dispersed reference beam, the electrical signals comprised of data indicative of a spectra of the sample beam after it exits the sample path and a spectra of the reference beam after it exits the reference path.

BRIEF DESCRIPTION OF THE DRAWINGS

The foregoing and other aspects of the exemplary embodiments of this invention are made more evident in the following Detailed Description, when read in conjunction with the attached Drawing Figures, wherein.

DETAILED DESCRIPTION

Of particular interest herein is a spectroscopic method that can be referred to as differential infrared (IR) spectroscopy, where IR energy is simultaneously passed through a sample material and through a reference material and is detected.

Figure 1:
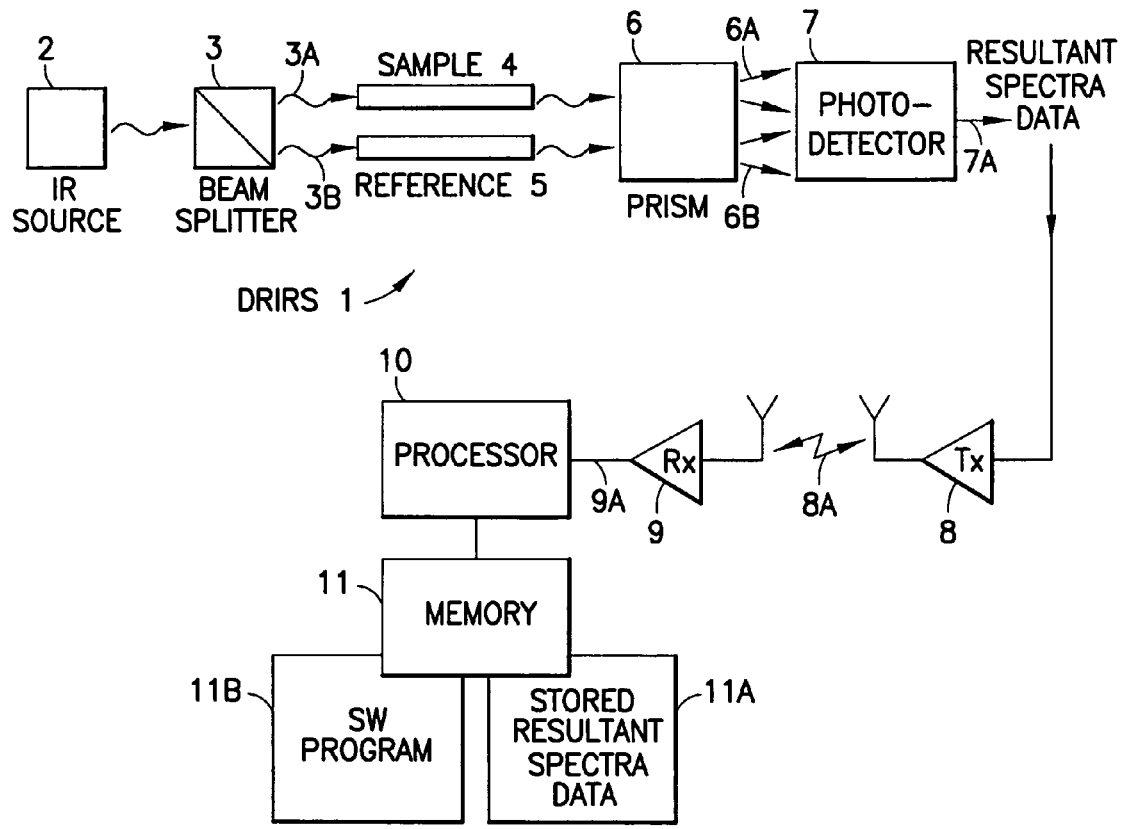
FIG. 1 is schematic depiction of an embodiment of a differential referential IR spectroscope in accordance with the exemplary embodiments of this invention.

Referring to FIG. 1, in accordance with the exemplary embodiments of this invention a differential referential IR spectroscope (DRIRS) 1 includes a broad spectrum IR source 2 and a beam splitter 3 that provides a sample beam 3A and a reference beam 3B. The sample beam 3A is applied to a sample path or leg 4 and the reference beam 3B is applied to a reference path or leg 5. The sample leg 4 contains a gas (e.g., air) containing an unknown sample of some chemical compound to be detected (e.g., $NO_x$ or some other chemical compound that may be found in ambient air). The reference leg 5 contains a known reference gas. After the sample beam 3A and the reference beam 3B pass through the sample leg 4 and the reference leg 5, respectively, they are applied to a wavelength dispersion element 6 such as a dispersive prism. The resulting dispersed sample spectra 6A and dispersed reference spectra 6B are then applied to a photodetector 7, such as a complementary metal oxide semiconductor (CMOS) or charge coupled device (CCD) linear or area array of photodetectors, where the dispersed sample spectra 6A and the dispersed reference spectra 6B are recorded and converted into electrical signals that can be readout and treated as resultant spectral data 7A.

In one exemplary embodiment the resultant (raw) spectra data 7A can be input to a transmitter (Tx) 8 and sent by a wired and/or a wireless link 8A to a remote receiver (Rx) 9 and then provided to a data processor 10 for analysis. The link 8A can be any suitable link or combination of links, such as a USB link, a Bluetooth™ link, and/or a cellular link, as three non-limiting examples of data connection links. For example, a Bluetooth™ link can be used to input the resultant spectra data 7A to a cellular phone, which in turn is connected via a cellular link to a telecommunications network and thence to a data communications network, such as the Internet, for providing the resultant spectra data to the data processor 10. The data processor 10 is connected with at least one memory 11 where resultant spectra data can be stored 11A as files or in any convenient form. The at least one memory 11 also includes at least one software (SW) program 11B configured to algorithmically process the stored resultant spectra data 11A. Note that the link 9A between the Rx 9 and the processor 10 can thus include one or more data communication networks, including the Internet.

In another exemplary embodiment the resultant (raw) spectra data 7A can be processed internally to the DRIRS 1, and just the result (e.g., an identification of a detected chemical species or compound or compounds in the sample gas) can be transmitted to a remote location. In this case then the data processor 10, memory 11, stored resultant spectra data 11A and SW program 11B can all be internal to the DRIRS 1 (e.g., between the output of the photodetector 7 and the input to the transmitter 8).

Figure 2:
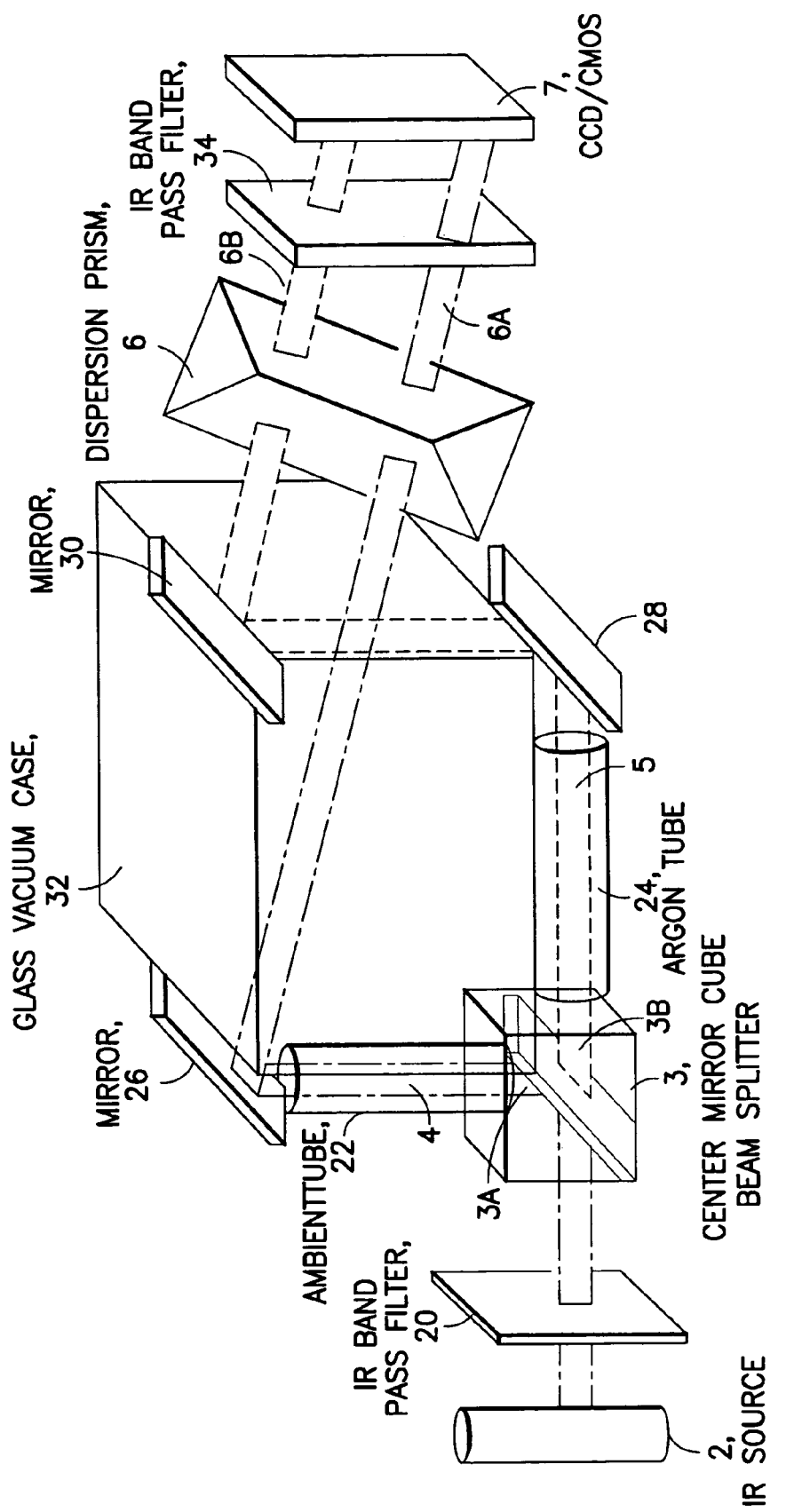
FIG. 2 is more detailed depiction of an embodiment of the differential referential IR spectroscope in accordance with the exemplary embodiments of this invention.

Reference is now made to FIG. 2 for showing in greater detail an exemplary and non-limiting embodiment of the differential referential IR spectroscope (DRIRS) 1.

In FIG. 2 the spectra infrared energy output from the source 2, a broad spectrum undercurrent xenon discharge tube or other intense IR source, passes through an IR bandpass filter 20 and is applied to the beam splitter 3. In one non-limiting example the IR source 2 outputs wavelengths in the range of about 2500 nm to about 6000 nm. The beam splitter 3 can be embodied as a center mirror cube beam splitter and provides substantially equal IR energy to the beams 3A and 3B. One of the IR beams 3A is passed through the gaseous sample 4. The sample 4 may be ambient air that is allowed to enter an end-closed but length-open tube 22 (e.g., a first glass tube). The other IR beam 3B is sent down the similar length reference path leg through the reference gas (e.g., Argon) contained in an end-closed and length-closed tube 24 (e.g., another glass tube of similar length as the first glass tube). The Argon in the tube 24 is used as a reference gas to compute a differential spectroscopic analysis of the gas contents of the open ambient tube 22.

Having traversed the length of the sample tube 22 and the reference tube 24 the beam 3A and the beam 3B are applied to mirror 26 and to mirrors 28, 30, respectively. The mirrors 26, 28 and the mirror 30 are used to direct the IR energy down identical path lengths and serve to fold the beam paths such that both beams 3A, 3B can be applied to dispersion prism 6 which is used to disperse the two IR beams according to their respective wavelengths. The beams 3A, 3B are preferably folded within an evacuated case 32, e.g., a glass case, to ensure that the beams are only encountering molecular species whilst traveling through the ambient sample tube 22 and the reference (argon) tube 24. That is, any interaction of the sample and reference beams 3A, 3B with an IR-absorbing chemical species occurs only along the known lengths of the tubes 22, 24. The two IR spectra 6A, 6B output from the prism 6 are directed through an IR bandpass filter 34 unto an unfiltered CCD or CMOS recording sensor 7 that captures the spectra of both the Argon gas and the sample gas and outputs the resultant spectra data 7A as shown in FIG. 1. The IR bandpass filters 34 and 20 are provided to remove any ambient non-IR light to which the photodetector 7 would typically respond.

The software 11B shown in FIG. 1 is employed by the data processor 10 to compute the constituent composition of the sample gas in the tube 22 by comparing the sample spectra against the known reference (Ar) spectra.

As has been described, the beam of IR light is produced and split into two separate beams 3A, 3B. One beam 3A is passed through the sample while the other beam 3B is passed through the known reference gas. Though there is a need at some point to compare the reference against a standard to enable calibration, this does not have to be performed in real time.

Infrared spectroscopy as used in accordance with the exemplary embodiments of this invention exploits the fact that molecules have specific frequencies at which they rotate or vibrate corresponding to discrete energy levels or vibration modes. The resonant frequencies are determined by the shape of the molecular potential energy surfaces, the masses of the atoms and by the associated vibration coupling. In order for a vibration mode in a molecule to be IR active, the molecule must be associated with changes in the permanent dipole. In particular, in the Born-Oppenheimer and harmonic approximations, i.e., when the molecular Hamiltonian corresponding to the electronic ground state can be approximated by a harmonic oscillator in the neighborhood of the equilibrium molecular geometry, the resonant frequencies are determined by the normal modes corresponding to the molecular electronic ground state potential energy surface.

Simple diatomic molecules have only a single bond which may stretch. More complex molecules have many bonds and vibrations can be conjugated leading to infrared absorptions at characteristic frequencies that may be related to chemical groups.

The IR spectrum of a sample that is generated by the apparatus shown in FIGS. 1 and 2 can thus be examined to reveal how much energy was absorbed and/or transmitted by the sample gas at each wavelength. The transmittance or absorption spectra allow the computation of the characteristics of the sample gas.

The use of the broad spectrum IR source 2 eliminates a need to use multiple monochromatic wavelengths. In some conventional IR approaches a Fourier transform is performed to allow the measurement of all the wavelengths at once. However, in the differential-referential approach in accordance with the exemplary embodiments of this invention the IR energy is not passed through an interferometer. By not generating an interferogram there is no need to compute the Fourier transform.

As gases typically exhibit a relatively weak absorbance to IR radiation a path length of, for example, approximately 5 cm can be used for both the sample tube 22 and the reference (Ar) tube 24.

It should be appreciated that the exemplary embodiments of the DRIRS 1 are not limited to only the features discussed above. For example, the undercurrent Xenon discharge tube used as the IR source 2 can be replaced by, as several non-limiting examples, a halogen IR source, a Group III-V semiconductor device such as a GaAlAs IR emitter, a laser diode, a light emitting diode or a nitrogen (air) arc lamp. A suitable correction for emission bandwidth can be implemented in software.

The reference gas is selected to be Argon as the three principle constituents of air are N 78%, O 21% and Ar 0.93%. In general, Argon is relatively inexpensive to obtain from air liquefaction. However, in other embodiments another substantially non-reactive gas may be used in the reference leg 5 in place of Argon.

It was noted above that the sample and reference tubes 22, 24 are each at least about 5 cm in length to allow sufficient sample molecules to be exposed to the IR energy. However, sample and reference tubes having lengths shorter than about 5 cm can also be used, with a corresponding increase in the IR energy output from the source 2. Sample and reference tubes 22, 24 longer than about 5 cm can also be used.

Two elongated regions of the CCD/CMOS detector 7 are exposed to the two dispersed IR beams 6A, 6B. The software/algorithms 11B (whether internal to the DRIRS 1 or external to the DRIRS 1) are programmed with the "true" spectra of the reference gas, such as Ar. This is done to allow detection and correction for spectral changes due to properties of the IR source 2, such as voltage emission bandwidth, aging, dirty optics and so forth. The reading of the reference gas allows for the application of spectra corrections. Hence the differential aspect of the DRIRS 1 arises from the use of a standard gas, e.g., Argon, to determine a difference spectra, and the referential aspect of the DRIRS 1 arises from the fact that the signal processor (the processor 10 shown in FIG. 1), is programmed with a standard emission allowing calibration of the reference spectra.

Figure 3:
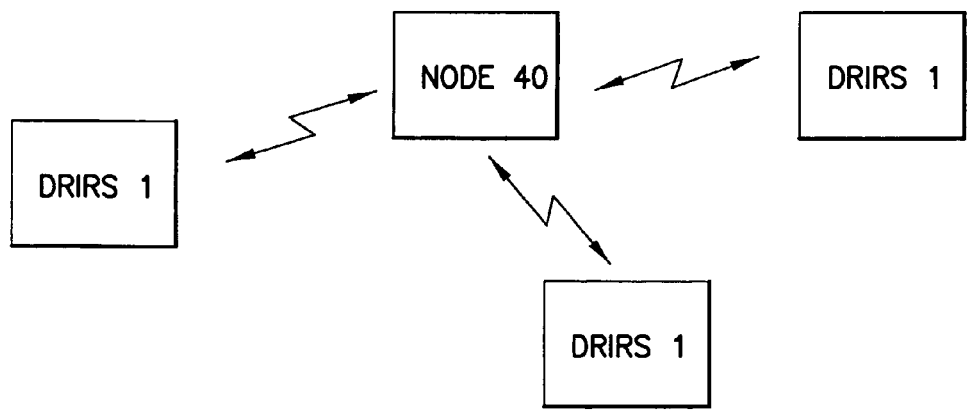
FIG. 3 shows a population of differential referential IR spectroscopes, as shown in FIGS. 1 and 2 that are in communication with a central node.

FIG. 3 shows a population of the DRIRS 1, as shown in FIGS. 1 and 2 that are in communication with a central node 40. The DRIRS 1 can be dispersed over a large geographical area and communicate with the central node 40 via wired and/or wireless communication links For the embodiment shown in FIG. 1 the individual DRIRS 1 can each communicate the raw resultant spectra data 7A that is then processed at the central node 40. In this case the data processor 10 and memory 11 may be resident at the central node 40. Alternatively the individual DRIRS 1 can each communicate the result of locally processing the resultant spectra data 7A, for the case where the data processor 10 and memory 11 are resident within each DRIRS 1. Individual ones of the DRIRS 1 can be fixed in place, such as being installed atop a building or some other structure, and communicate via a wired or wireless connection. Alternatively one or more of the DRIRS 1 can be mounted to a mobile platform and communicate via a wireless connection. In this case a suitable location determining apparatus (e.g., a GPS receiver) can be included with the DRIRS 1 or the mobile platform, and current location data transmitted as well to the central node 40.

As should be appreciated, one considerable technical effect and technical advantage that arises from the use of the exemplary embodiments is that there is provided a technique to produce inexpensive spectra of air or other gaseous compounds that can be evaluated for components such as airborne contaminants or pollutants. In that the DRIRS 1 need contain no moving parts (e.g., scanning mirrors and the like) it can be made inherently rugged and suitable for field use in extreme environments. Further, by the use of the reference gas leg 5 the DRIRS 1 can be considered as being essentially self-calibrating, thus eliminating a need to often perform field service and calibration tasks.

Based on the foregoing it should be apparent that the exemplary embodiments of this invention provide a method, apparatus and computer program(s) to detect a presence of one or more chemical compounds in an ambient gas mixture.

Figure 4:
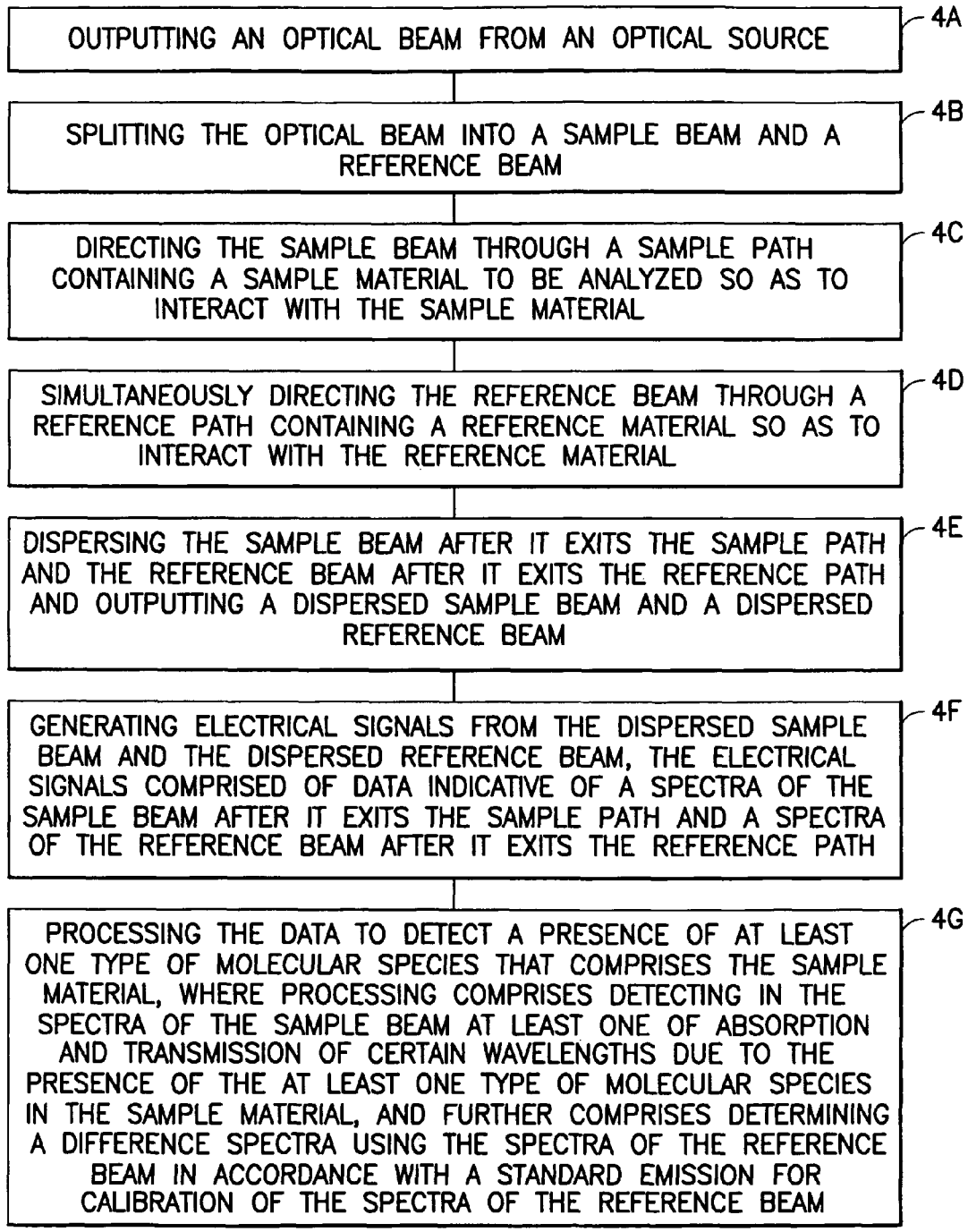
FIG. 4 is a logic flow diagram that illustrates the operation of a method in accordance with the exemplary embodiments of this invention.

FIG. 4 is a logic flow diagram that illustrates the operation of a method in accordance with the exemplary embodiments of this invention. At Block 4A the method performs a step of outputting an optical beam from an optical source. At Block 4B the method performs splitting the optical beam into a sample beam and a reference beam. At Block 4C the method performs directing the sample beam through a sample path containing a sample material to be analyzed so as to interact with the sample material. At Block 4D the method performs simultaneously directing the reference beam through a reference path containing a reference material so as to interact with the reference material. At Block 4E the method performs dispersing the sample beam after it exits the sample path and the reference beam after it exits the reference path and outputting a dispersed sample beam and a dispersed reference beam. At Block 4F the method performs generating electrical signals from the dispersed sample beam and the dispersed reference beam, the electrical signals comprised of data indicative of spectra of the sample beam after it exits the sample path and a spectra of the reference beam after it exits the reference path. At Block 4G the method further performs processing the data to detect a presence of at least one type of molecular species that comprises the sample material where processing comprises detecting in the spectra of the sample beam at least one of absorption and transmission of certain wavelengths due to the presence of the at least one type of molecular species in the sample material, and further comprises determining a difference spectra using the spectra of the reference beam in accordance with a standard emission for calibration of the spectra of the reference beam.

In the method of the preceding paragraphs, where the sample material comprises air, and where the reference material comprises a constituent component of air, such as Argon.

In the method of the preceding paragraphs, where the optical source is a broadband infrared source, and may have wavelengths in a range of about 2500 nm to about 6000 nm.

In the method of the preceding paragraphs, where dispersing uses a dispersive prism, and where generating electrical signals comprises operating a charge coupled device array of photodetectors or a complementary metal oxide semiconductor array of photodetectors.

In the method of the preceding paragraphs, where the sample path comprises a sample tube that is open to the environment for receiving ambient air, where the reference path comprises a sealed reference tube that contains Argon, and where a length of the sample tube is equal to the length of the reference tube.

The various blocks shown in FIG. 4 may be viewed as method steps, and/or as operations that result from operation of computer program code, and/or as a plurality of coupled logic circuit elements constructed to carry out the associated function(s).

The exemplary embodiments also provide an apparatus that includes an optical source providing an optical beam; a splitter configured to split the optical beam into a sample beam and a reference beam; a sample path containing a sample material to be analyzed, the sample beam being directed through the sample path so as to interact with the sample material; a reference path containing a reference material, the reference beam being directed through the reference path so as to interact with the reference material; a disperser configured to receive the sample beam after it exits the sample path and to receive the reference beam after it exits the reference path, the disperser outputting a dispersed sample beam and a dispersed reference beam; and a photodetector disposed to receive the dispersed sample beam and the dispersed reference beam and outputting electrical signals comprised of data indicative of a spectra of the sample beam after it exits the sample path and a spectra of the reference beam after it exits the reference path.

In one exemplary embodiment the apparatus further includes a data processor connected with a memory storing a software program configured to process the data to detect a presence of at least one type of molecular species that comprises the sample material; and a transmitter configured to transmit the processed data to a receiver. In another exemplary embodiment the apparatus comprises a transmitter configured to transmit the data to a remote receiver for processing.

The exemplary embodiments also provide an apparatus that includes means for outputting an optical beam from an optical source; means for splitting the optical beam into a sample beam and a reference beam; means for directing the sample beam through a sample path containing a sample material to be analyzed so as to interact with the sample material; means for simultaneously directing the reference beam through a reference path containing a reference material so as to interact with the reference material; means for dispersing the sample beam after it exits the sample path and the reference beam after it exits the reference path and for outputting a dispersed sample beam and a dispersed reference beam; and means for generating electrical signals from the dispersed sample beam and the dispersed reference beam, where the electrical signals are comprised of data indicative of a spectra of the sample beam after it exits the sample path and a spectra of the reference beam after it exits the reference path.

In general, the various exemplary embodiments may be implemented in hardware or special purpose circuits, software, logic or any combination thereof. For example, some aspects may be implemented in hardware, while other aspects may be implemented in firmware or software which may be executed by a controller, microprocessor or other computing device, although the invention is not limited thereto. While various aspects of the exemplary embodiments of this invention may be illustrated and described as block diagrams, flow charts, or using some other pictorial representation, it is well understood that these blocks, apparatus, systems, techniques or methods described herein may be implemented in, as non-limiting examples, hardware, software, firmware, special purpose circuits or logic, general purpose hardware or controller or other computing devices, or some combination thereof.

It should thus be appreciated that at least some aspects of the exemplary embodiments of the inventions may be practiced in various components such as integrated circuit chips and modules, and that the exemplary embodiments of this invention may be realized in an apparatus that is embodied as an integrated circuit. The integrated circuit, or circuits, may comprise circuitry (as well as possibly firmware) for embodying at least one or more of a data processor or data processors, a digital signal processor or processors, baseband circuitry and radio frequency circuitry that are configurable so as to operate in accordance with the exemplary embodiments of this invention.

Various modifications and adaptations to the foregoing exemplary embodiments of this invention may become apparent to those skilled in the relevant arts in view of the foregoing description, when read in conjunction with the accompanying drawings. However, any and all modifications will still fall within the scope of the non-limiting and exemplary embodiments of this invention. For example, optical sources that output other than IR light may be used. Further by example, while described in the context of the analysis of a gas (e.g., ambient air), in other embodiments the sample tube 22 could contain a sample liquid that is flowed through the tube (e.g., effluent water), while the reference tube 24 could contain a reference liquid (e.g., sterile, distilled water). In such alternative embodiments the optical source 2 can be modified/selected so as to provide a range of wavelengths (and an output power) suitable for use with the sample material and the selected reference material.

It should be noted that the terms "connected," "coupled," or any variant thereof, mean any connection or coupling, either direct or indirect, between two or more elements, and may encompass the presence of one or more intermediate elements between two elements that are "connected" or "coupled" together. The coupling or connection between the elements can be physical, logical, or a combination thereof. As employed herein two elements may be considered to be "connected" or "coupled" together by the use of one or more wires, cables and/or printed electrical connections, as well as by the use of electromagnetic energy, such as electromagnetic energy having wavelengths in the radio frequency region, the microwave region and the optical (both visible and invisible) region, as several non-limiting and non-exhaustive examples.

Further, some of the features of the various non-limiting and exemplary embodiments of this invention may be used to advantage without the corresponding use of other features. As such, the foregoing description should be considered as merely illustrative of the principles, teachings and exemplary embodiments of this invention, and not in limitation thereof.

What is claimed is:

1. An apparatus, comprising:
an optical source providing an optical beam;
a splitter configured to split the optical beam into a sample beam and a reference beam;
a sample path containing a sample material to be analyzed, said sample beam being directed through said sample path so as to interact with said sample material;
a reference path containing a reference material, said reference beam being directed through said reference path so as to interact with said reference material;
a disperser configured to receive said sample beam after it exits the sample path and to receive said reference beam after it exits the reference path, said disperser outputting a dispersed sample beam and a dispersed reference beam;
a photodetector disposed to receive the dispersed sample beam and the dispersed reference beam and to output a first electrical signal comprised of data indicative of a spectra of the sample beam after it exits the sample path and a second electrical signal comprised of data indicative of a spectra of the reference beam after it exits the reference path; and a data processor configured to compare the first electrical signal to a predetermined reference value to calibrate the second electrical signal.

2. The apparatus of claim 1, where said data processor is connected with a memory storing a software program configured to process the data to detect a presence of at least one type of molecular species that comprises the sample material; and a transmitter configured to transmit the processed data to a receiver.

3. The apparatus of claim 2, where said data processor is further configured to detect in the spectra of the sample beam at least one of absorption and transmission of certain wavelengths due to the presence of the at least one type of molecular species in the sample material, and is further configured to determine a difference spectra using the spectra of the reference beam in accordance with a standard emission for calibration of the spectra of the reference beam.

4. The apparatus of claim 1, further comprising a transmitter configured to transmit the data to a remote receiver.

5. The apparatus as in claim 1, where the sample material comprises air, and where the reference material comprises a constituent component of air.

6. The apparatus as in claim 1, where the sample material comprises air, and where the reference material comprises Argon.

7. The apparatus as in claim 1, where the optical source is a broadband infrared source.

8. The apparatus as in claim 1, where the optical source is an infrared source having wavelengths in a range of about 2500 nm to about 6000 nm.

9. The apparatus as in claim 1, where said disperser is comprised of a dispersive prism, and where said photodetector is comprised of a charge coupled device array of photodetectors or a complementary metal oxide semiconductor array of photodetectors.

10. The apparatus as in claim 1, where the sample path comprises a sample tube that is open to the environment for receiving ambient air, where the reference path comprises a sealed reference tube that contains Argon, and where a length of the sample tube is equal to the length of the reference tube.

11. A method, comprising:
outputting an optical beam from an optical source;
splitting the optical beam into a sample beam and a reference beam;
directing the sample beam through a sample path containing a sample material to be analyzed so as to interact with said sample material;
simultaneously directing the reference beam through a reference path containing a reference material so as to interact with said reference material;
dispersing said sample beam after it exits the sample path and said reference beam after it exits the reference path and outputting a dispersed sample beam and a dispersed reference beam;
generating a first electrical signal and a second electrical signal from said dispersed sample beam and said dispersed reference beam, respectively, the first electrical signal comprised of data indicative of a spectra of the sample beam after it exits the sample path and the second electrical signal comprised of data indicative of a spectra of the reference beam after it exits the reference path; and
comparing the first electrical signal to a predetermined reference value to calibrate the second electrical signal.

12. The method of claim 11, further comprising:
processing the data to detect a presence of at least one type of molecular species that comprises the sample material; and transmitting the processed data to a receiver.

13. The method of claim 12, where processing comprises detecting in the spectra of the sample beam at least one of absorption and transmission of certain wavelengths due to the presence of the at least one type of molecular species in the sample material, and further comprises determining a difference spectra using the spectra of the reference beam in accordance with a standard emission for calibration of the spectra of the reference beam.

14. The method of claim 11, further comprising transmitting the data to a remote receiver.

15. The method of claim 11, where the sample material comprises air, and where the reference material comprises a constituent component of air.

16. The method of claim 11, where the sample material comprises air, and where the reference material comprises Argon.

17. The method of claim 11, where the optical source is a broadband infrared source.

18. The method of claim 11, where the optical source is an infrared source having wavelengths in a range of about 2500 nm to about 6000 nm.

19. The method of claim 11, where dispersing uses a dispersive prism, and where generating electrical signals comprises operating a charge coupled device array of photodetectors or a complementary metal oxide semiconductor array of photodetectors.

20. The method of claim 11, where the sample path comprises a sample tube that is open to the environment for receiving ambient air, where the reference path comprises a sealed reference tube that contains Argon, and where a length of the sample tube is equal to the length of the reference tube.

* * * * *